United States Patent [19]

Stüttgen et al.

[11] 4,390,532
[45] Jun. 28, 1983

[54] TOPICAL COMBINATIONS OF AN α-ESTRADIOL WITH A METHYL XANTHINE

[75] Inventors: Günter Stüttgen; Hans Schaefer, both of Berlin, Fed. Rep. of Germany

[73] Assignee: Dr. Carl Hahn, G.m.b.H., Dusseldorf, Fed. Rep. of Germany

[21] Appl. No.: 884,452

[22] Filed: Mar. 8, 1978

Related U.S. Application Data

[63] Continuation of Ser. No. 750,086, Dec. 13, 1976, abandoned, which is a continuation-in-part of Ser. No. 509,369, Sep. 26, 1974, abandoned.

[30] Foreign Application Priority Data

Oct. 6, 1973 [DE] Fed. Rep. of Germany ....... 2350315

[51] Int. Cl.³ ................. A61K 31/56; A61K 31/70; A61K 31/52
[52] U.S. Cl. .................................. 424/240; 424/180; 424/183; 424/253
[58] Field of Search .................. 424/240, 253, 180

[56] References Cited

U.S. PATENT DOCUMENTS 3,826,834 7/1974 Reiches ............................. 424/263

OTHER PUBLICATIONS

Lubow, Chem. Abst., vol. 84, (1976), p. 79595p.
Tardy et al., Chem. Abst., vol. 75, (1971), p. 133,013b.
Korshunova, Chem. Abst., vol. 68, (1968), p. 85876s.
Alexander, Amer. Perf. & Cosmet., vol. 82, (Sep. 1967), pp. 31, 36, 37 & 38.
Pincus et al. The Hormones, vol. 1, (1948), pp. 366 & 367.

Primary Examiner—Douglas W. Robinson
Attorney, Agent, or Firm—Benjamin F. Lambert

[57] ABSTRACT

Topical compositions comprising an active ingredient selected from at least two of the following three classes of compounds:
- (a) N-methyl-substituted xanthines containing at least two methyl substituents;
- (b) α-estradiol and certain derivatives thereof; and
- (c) the mucopolysaccharides have surprisingly beneficial effects on the skin and the scalp. These compositions may be prepared in the form of lotions, emulsions, ointments, gels and like forms for topical administration, and may be used to treat such conditions as acne, wrinkles, and androgen baldness.

12 Claims, No Drawings

TOPICAL COMBINATIONS OF AN α-ESTRADIOL WITH A METHYL XANTHINE

CROSS-REFERENCE TO RELATED APPLICATION

This application is a continuation of our copending application Ser. No. 750,086, filed on Dec. 13, 1976, now abandoned, which application is in turn a continuation-in-part of our application Ser. No. 509,369, filed Sept. 26, 1974, now abandoned.

BACKGROUND OF THE INVENTION

The present invention relates to compositions for topical application, and more particularly to such compositions useful in the treatment of androgen baldness as well as skin wrinkles and acne.

Because the topical treatment of baldness has in the past acquired a reputation of quackery, the area of utility of the present invention in respect to baldness is carefully circumscribed. Common baldness in men, also known as "male pattern baldness" may be considered a physiological reaction in persons having a tendency towards this type of baldness. The main factor which causes this type of baldness in such persons is the presence of the male sex hormone, testosterone, from which arises the designation "androgen" meaning dependent upon male factors. Androgen baldness also occurs in women.

It is not claimed that this type of baldness can always be reversed or that hair can be caused to grow again on a bald scalp. Where the hair folicles have already degenerated and are no longer producing pigmented hairs, no method or treatment is presently known which will reverse this process. In contrast, however, where the process of degeneration has only just begun, if an adequate treatment can be found to arrest or retard the degeneration process, baldness can be prevented or at least mitigated.

It has long been known that the androgen baldness process in men can be favorably influenced through the application of female hormones, especially estrogens. See for example, German patent application 23 50 315.3 and British Pat. No. 720,561. However, the risk of irreversible side effects such as changes in the voice, swelling of the breasts, and reduced sexual potency associated with the application of female hormones has been a severe disadvantage associated with this therapy.

Even where these risks have been accepted and estrogens have been applied, there does not appear to have been any decrease, much less a cessation, in the loss in hair. See, for example, H. Wustner and C. E. Orfanos-"Alopecia Androgenetica and its Local Treatment Using Preparations for External Treatment Containing Estrogens and Corticosteroids," Z Hautkr. 49 (20) 879-888 (1974). Even where estrogens have been found effective in the treatment of androgen baldness, only those estrogens having very low estrogenic activity have been suggested. See, for example, U.S. Pat. No. 3,729,560.

It is an object of the present invention to provide a composition for topical treatment of androgen baldness which has greater efficacy than those previously suggested.

It is a further object to provide such a composition which has no sexual effect.

It is also an object to provide topical compositions for treatment of acne and skin wrinkles.

SUMMARY OF THE INVENTION

The present invention relates to new topical preparations comprising effective combined amounts of active ingredients selected from at least two of the following three classes of compounds:

(a) compounds of the general formula I

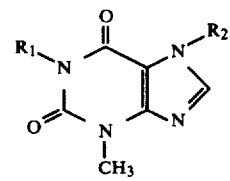

wherein $R_1$ and $R_2$ each represent hydrogen or the methyl group and at least one of the substituents $R_1$ and $R_2$ is a methyl group, (b) α-estradiol derivatives of the general formula II

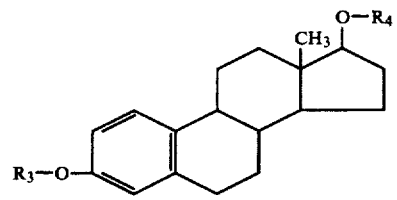

wherein each of $R_3$ and $R_4$, which may be identical or different from each other, represents hydrogen, a fatty acyl group having from 1 to 18 carbon atoms, the phenyl group or the group $-SO_3Me$, Me being the cation of an alkali metal, and (c) mucopolysaccharides.

The term "effective combined amounts" as used herein means amounts of the active ingredients which, when combined in the claimed compositions, are effective to produce the desired result, e.g. alleviation of reversible androgen baldness. Since the claimed compositions require at least two active ingredients, it should be understood that an "effective amount" of one ingredient will not produce the desired result unless combined with an "effective amount" of at least one other active ingredient.

Preferably the combination preparations according to the present invention contain the compound of formula I in an amount ranging from 0.01 to 1.2% by weight, contain the compound of formula II in an amount ranging from 0.005 to 0.1% by weight and contain the mucopolysaccharide in an amount ranging from 0.01 to 5.0% by weight.

DESCRIPTION OF THE PREFERRED EMBODIMENTS

The active substances of the combination preparations for external application according to the present invention are mostly known. The compounds of the general formula I represent the xanthines caffeine, theobromine and theophylline. The compound of formula II wherein $R_1$ and $R_2$ both represent hydrogen is the known product α-estradiol. This compound is the sexually nonspecific form of the estrogen estradiol, as opposed to the sexually-specific β form. The compounds of formula II wherein $R_1$ or $R_2$ is other than hydrogen are derivatives of α-estradiol. The mucopolysaccharides are preferably represented by the heparins and heparinoides, such as hyaluronic acid and chondroitin sulfuric acid, including chondroitine sulphate A and B.

The new combination preparations according to the present invention are characterized by surprisingly beneficial effects on the skin and in particular on the scalp. Compositions comprising a compound of formula I and a compound of formula II have been found to be surprisingly useful in the treatment of androgen baldness. Compositions comprising a compound of formula II and a mucopolysaccharide have been found to be surprisingly useful in the treatment of skin wrinkles.

Those topical preparations according to the present invention are preferred wherein the xanthine is 1,3,7-trimethyl xanthine (caffeine), the α-estradiol derivative is a compound of formula II wherein $R_3$ and $R_4$ represent hydrogen or an alkanoyl group having from 2 to 7 carbon atoms, in particular the acetyl group, or the group —$SO_3Na$, and the mucopolysaccharide is heparin.

Besides the above active ingredients, the combination preparations according to the present invention further comprise the usual vehicles, diluents and/or solvents used in the preparation of pharmaceutical and cosmetic preparations for external use. The preparations according to the present invention may be in the form of aqueous-alcoholic lotions, water-in-oil emulsions (w/o emulsions), oil-in-water-emulsions (o/w emulsions), ointments, or gels. For treating androgen baldness, aqueous-alcoholic lotions containing compounds of both formula I and II are preferably used; for the treatment of skin wrinkles, the above emulsions, ointments and gels are preferably used which contain compounds of formula II in combination with mucopolysaccharides alone or together with a xanthine of formula I. For the treatment of acne, alcoholic gels are used which contain compounds of formula I and II.

The combination preparations according to the present invention may further contain perfumes and/or dyestuffs. They may also contain other active substances producing additional effects, in particular cholesterol, lecithin, nucleic acids, pyrimidines, purines and/or vitamins.

The preparations according to the present invention are prepared by the usual processes. Their pH is buffered to a value optimal for the intended use by means of appropriate buffering systems such as disodiumphosphate/monopotassiumphosphate (phosphate buffer) or sodium lactate/lactic acid (lactate buffer). The optimal pH range for preparations to be applied on the scalp is 6.0 to 7.0 and for those to be applied on the skin is 5.4 to 5.8.

The following examples serve to further illustrate the present invention. The conservation agents, (preservatives) Nipastat ® and Phenonip ® referred to below are products of Nipa Laboratories, London, England. The conservation agent Bronopol is 2-bromo-2-nitropropan-1,3-diol.

EXAMPLE I

Preparation of alcoholic-aqueous lotions containing caffeine and α-estradiol

| | Parts by Weight |
|---|---|
| (a) Components | |
| Caffeine | 0.18 |
| α-Estradiol | 0.008 |
| Isopropanol | 35. |
| Dexadecyl alcohol | 0.1 |
| Protein hydrolysate | 0.1 |
| Conservation agent | 0.3 |
| Distilled water filled up to total weight of | 100. |
| (b) Components | |
| Caffeine | 0.22 |
| α-Estradiol | 0.012 |
| Isopropanol | 60. |
| Hexadecyl alcohol | 0.5 |
| Portein hydrolysate | 5.0 |
| Conservation agent | 0.3 |
| Distilled water filled up to total weight of | 100. |

The components are completely dissolved in the isopropanol and a substantial amount of distilled water, and distilled water is filled up to 100% by weight.

EXAMPLE II

Preparation of a w/o-emulsion containing α-estradiol and α-heparin.

| | Parts by Weight |
|---|---|
| (a) Components | |
| α-Estradiol | 0.008 |
| α-Heparin | 0.12 |
| Mixture of higher molecular weight esters, consisting to the greatest extent of mixed esters pentaerythritol fatty acid ester and citric acid alkyl ester | 7.0 |
| Peanut oil | 10.0 |
| Oleic acid decyl ester | 5.0 |
| Beeswax, white | 0.8 |
| Vaseline, white | 19.0 |
| n-Octadecanol | 3.0 |
| α-Tocopherol (antioxidant) | 0.05 |
| Phenonip (conversion agent) | 0.3 |
| Dimineralized water filled up to a total weight of | 100. |
| (b) Components | |
| α-Estradiol | 0.012 |
| α-Heparin | 0.18 |
| Mixture of higher molecular weight esters, consisting to the greatest extent of mixed esters pentaerythritol fatty acid ester and citric acid alkyl ester | 8.0 |
| Peanut oil | 20.0 |
| Oleic acid decyl ester | 4.0 |
| Beeswax, white | 2.0 |
| Vaseline, white | 9.0 |
| n-Octadecanol | 5.0 |
| α-Tocopherol (antioxidant) | 0.05 |
| Phenonip (conservation agent) | 0.3 |
| Demineralized water filled up to a total weight of | 100. |

The components are thoroughly mixed with the water-free oily components. Thereafter, the demineralized water is admixed with vigorous mechanical stirring.

EXAMPLE III

Production of an o/w emulsion containing α-estradiol and α-heparin.

| (a) Components | Parts by Weight |
|---|---|
| α-Estradiol | 0.008 |
| α-Heparin | 0.12 |
| Ethoxylated cetyl stearyl alcohol having about 12 molecules of ethylene oxide per alcohol molecule | 2. |
| Mixture of mono- and diglycerides of palmitic and stearic acids | 12. |
| 2-Octyldodecanol | 10. |
| Caprylic caprinic acid triglyceride | 15. |
| 1,2-Propylene glycol | 5. |
| Nipastat (conservation agent) | 0.18 |
| Demineralized water filled up to a total weight of | 100. |
| (b) Components | |
| α-Estradiol | 0.012 |
| α-Heparin | 0.17 |
| Ethoxylated cetyl stearyl alcohol having about 12 molecules of ethylene oxide per alcohol molecule | 3. |
| Mixture of mono- and diglycerides of palmitic and stearic acids | 3. |
| 2-Octyldodecanol | 15. |
| Caprylic caprinic acid triglyceride | 15. |
| 1,2-Propylene glycol | 20. |
| Nipastat (conservation agent) | 8. |
| Demineralized water filled up to a total weight of | 0.5 |
| | 0.18 |
| | 100. |

The components are mixed as described in Example II.

EXAMPLE IV

Preparation of a water-free (non-aqueous) ointment containing α-estradiol diacetate and α-heparin.

| | Parts by Weight |
|---|---|
| (a) Components | |
| α-Heparin | 0.12 |
| α-Estradiol diacetate | 0.01 |
| Glycerine monostearate | 12.0 |
| Ethoxylated cetyl stearyl alcohol having about 20 molecules of ethylene oxide per alcohol molecule | 2.5 |
| Cholesterol | 0.8 |
| Lecithin | 0.8 |
| α-Tocopherol (antioxidant) | 0.05 |
| Oleic acid decylester filled up to a total weight of | 100. |
| (b) Components | |
| α-Heparin | 0.17 |
| α-Estradiol diacetate | 0.015 |
| Glycerine monostearate | 16.0 |
| Ethoxylated cetyl stearyl alcohol having about 20 molecules of ethylene oxide per alcohol molecule | 3.5 |
| Cholesterol | 1.0 |
| Lecithin | 1.0 |
| α-Tocopherol (antioxidant) | 0.18 |
| Oleic acid decylester filled up to a total weight of | 100. |

The components are thoroughly admixed in an ointment mill (a mill having three rollers made of hardened porcelain) until a homogeneous ointment is obtained.

EXAMPLE V

Preparation of a transparent gel containing caffeine, the sodium salt of α-estradiol sulphate, and α-heparin.

| | Parts by Weight |
|---|---|
| (a) Components | |
| Sodium salt of α-estradiol sulfate | 0.008 |
| α-Heparin | 0.17 |
| Caffeine | 0.4 |
| Ethoxylated cetyl stearyl alcohol having about 30 molecules of ethylene oxide per alcohol molecule | 11.0 |
| Polyol fatty acid ester | 18.0 |
| Palmitic acid isopropyl ester | 6.0 |
| Lecithin | 0.8 |
| Nipastat (conservation agent) | 0.2 |
| Distilled water filled up to a total weight of | 100. |
| (b) Components | |
| Sodium salt of α-estradiol sulphate | 0.010 |
| α-Heparin | 0.25 |
| Caffeine | 0.6 |
| Ethoxylated cetyl stearyl alcohol having about 30 molecules of ethylene oxide per alcohol molcule | 13.0 |
| Polyol fatty acid ester | 20.0 |
| Palmitic acid isopropyl ester | 4.0 |
| Lecithin | 1.1 |
| Nipastat (conservation agent) | 0.2 |
| Distilled water filled up to a total weight of | 100. |

Two thirds of the water phase are added to the fatty phase molten at about 90° C. at the same temperature. The resulting gel is cooled with stirring to about 50° C., the active agents are dissolved in, or suspended in the remaining amount of water and added to the gel. In order to avoid the admixture of air, the stirring is finished shortly after a homogeneous mixture is reached.

EXAMPLE VI

Preparation of a gel for the treatment of acne, containing caffeine and the sodium salt of α-estradiol sulphate.

| | Parts by Weight |
|---|---|
| (a) Components | |
| Sodium salt of α-estradiol sulphate | 0.01 |
| Caffeine | 0.8 |
| Ethoxylated cetyl stearyl alcohol having about 30 molecules of ethylene oxide per alcohol molecule | 11.0 |
| Polyol fatty acid ester | 18.0 |
| Palmitic acid isopropyl ester | 6.0 |
| Ethanol (70%) | 0.5 |
| Lecithin | 0.8 |
| Bronopol (conservation agent) | 0.02 |
| Distilled water filled up to a total weight of | 100. |
| (b) Components | |
| Sodium salt of α-estradiol sulphate | 0.07 |
| Caffeine | 1.1 |
| Ethoxylated cetyl stearyl alcohol having about 30 molecules of ethylene oxide per alcohol molecule | 13.0 |
| Polyol fatty acid ester | 20.0 |
| Palmitic acid isopropyl ester | 4.0 |
| Ethanol (70%) | 10.0 |
| Lecithin | 1.2 |
| Bronopol (conservation agent) | 0.02 |
| Distilled water filled up to a total weight of | 100. |

The gel is prepared as described in Example V.

EXAMPLE VII

Clinical testing of a composition of the invention to determine its usefulness for the alleviation and retarding of reversible androgen baldness was conducted as set forth below.

Compositions comprising about 0.05% α-estradiol and about 0.1% caffeine by weight were administered to out-patients over a period of about three years. While the preparations tested were not of identical composition throughout the entire period, a typical formula is given below:

| Ingredient | Percent W/W |
|---|---|
| caffeine | 0.10 |
| α-estradiol | 0.05 |
| isopropanol | 35.00 |
| hexadecyl alcohol | 0.10 |
| Nipastat ® (preservative) | 0.30 |
| distilled water | q. s. |
| | 100.00 |

The results of tests on 53 persons with a composition illustrated by the above are presented in the following Table I. The composition was applied in a single application of 3 ml/day over an area of approximately 200 cm² for at least six months in each case.

TABLE I

Treatment of loss of hair using a composition comprising 0.05% of 17 alpha-estradiol and 0.1% caffeine.

| | | male | female |
|---|---|---|---|
| Number of test persons: | 53 | 24 | 29 |
| (a) Trichogramm stage in the parietal region before treatment (arithmetic mean) | telogen stage | 30% | 40% |
| | growth stage | 55% | 50% |
| | variable | 15% | 10% |
| Trichogramm stage in the parietal region after a treatment of 6 to 24 months (arithmetic mean) | telogen stage | 35% | 30% |
| | growth stage | 60% | 65% |
| | variable | 5% | 5% |
| (b) Hair count (number of hairs counted by test persons as removed by combing in the morning) | before treatmt. (arith. mean) | 80 hairs | 60 hairs |
| | after treatment as described above (arith. mean) | 40 hairs | 40 hairs |
| (c) Number of test persons reporting stop of intensive loss of hair or considerable slow-down | | 18 test persons (after 3 months of treatment at the earliest) | 24 test persons (after 3 months of treatment at the earliest) |
| (d) Type of newly growing hair | lanugo hair | 15 | 5 |
| | vellus hair | 1 | 10 + |
| (e) Undesired side effects | | none | none |
| Desired | | | Decrease of a migraine observed by 3 patients |

+ of these, 3 after 20 treatments

The results in Table I demonstrate that this composition of the invention alleviates and retards reversible androgen baldness. There is shown a comparative increase in the number of hairs in a growth stage in men, while indicating in a more marked degree a decrease in the number of hairs in the telogen (resting or dead) stage and, simultaneously, an increase in the number of hairs in a growth stage in women. Moreover, this table demonstrates the pronounced decrease in the loss of hairs removed during combing, particularly in the case of men. The decrease or stop in the intensive loss of hair caused by the treatment with the composition of the invention was observed in 18 out of 24 (75%) of the male patients and in 24 out of 29 (85%) of the female patients. These surprisingly good results are superior to any obtained with prior art compositions.

None of the subjects of this test showed any unwanted local or systemic side affects.

The above examples have been provided for illustration only and not to restrict the scope of the present invention, which scope is defined by the appended claims.

What is claimed is:

1. A method for treating a subject suffering from reversible androgen baldness which comprises topically applying to the baldness site of said subject a composition comprising effective combined amounts of an α-estradiol compound and a methyl xanthine compound.

2. The method of claim 1 wherein the composition comprises from about 0.10% to about 1.2% by weight of caffeine and from about 0.005% to about 0.10% by weight of α-estradiol.

3. A topical composition comprising from about 0.005% to about 0.1% by weight of (a) an α-estradiol compound of the general formula

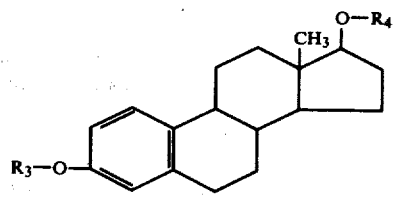

wherein $R_3$ and $R_4$, which may be identical or different from each other, represent hydrogen atoms, fatty acyl groups having from 1 to 18 carbon atoms, the phenyl group or the group —SO₃Me, Me being the cation of an alkali metal; in combination with from about 0.01% to about 1.2% by weight:

(b) methyl xanthine compounds of the general formula

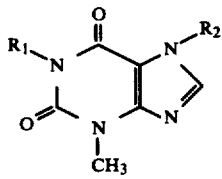

wherein $R_1$ and $R_2$ represent hydrogen atoms or the methyl group and at least one of the substituents $R_1$ and $R_2$ is the methyl group.

4. The composition of claim 3 which is useful for treatment of reversible androgen baldness and comprises from about; 0.005% to about 0.1% by weight of said α-estradiol compound and from about 0.01% to about 1.2% by weight of said methyl xanthine compound.

5. The composition of claim 4 wherein said α-estradiol compound is α-estradiol and said methyl xanthine is caffeine.

6. The composition of claim 4 in the form of an aqueous-alcoholic lotion.

7. The composition of claim 3 which is useful for treating acne and comprises from about 0.005% to about 0.1% by weight of said α-estradiol compound and from about 0.01% to about 1.2% of said methyl xanthine compound.

8. The composition of claim 7 in the form of an alcoholic gel.

9. The composition of claim 3 wherein said methyl xanthine compound is caffeine.

10. The composition of claim 3 wherein said methyl xanthine compound is selected from the group consisting of theobromine and theophylline.

11. The composition of claim 1 which comprises the sodium salt of α-estradiol sulphate, α-heparin and caffeine.

12. The composition of claim 7 which comprises the sodium salt of α-estradiol sulphate and caffeine.

* * * * *